(12) United States Patent
Boehm et al.

(10) Patent No.: US 10,568,747 B2
(45) Date of Patent: Feb. 25, 2020

(54) INSTRUMENT FOR INSERTING A SPINAL IMPLANT AND A SPINAL IMPLANT

(71) Applicant: MEDICON eG Chirurgiemechaniker-Genossenschaft, Tuttlingen (DE)

(72) Inventors: Heinrich Boehm, Weimar (DE); Andreas Burger, Tuttlinngen (DE); Gerd Widmaier, Tuttlingen (DE); Klaus Wenzler, Frittlingen (DE)

(*) Notice: Subject to any disclaimer, the term of this patent is extended or adjusted under 35 U.S.C. 154(b) by 203 days.

(21) Appl. No.: 15/652,476

(22) Filed: Jul. 18, 2017

(65) Prior Publication Data
US 2018/0021149 A1    Jan. 25, 2018

(30) Foreign Application Priority Data
Jul. 21, 2016  (DE) .................. 10 2016 113 488

(51) Int. Cl.
*A61F 2/46*     (2006.01)
*A61F 2/44*     (2006.01)
*A61F 2/30*     (2006.01)

(52) U.S. Cl.
CPC .......... *A61F 2/4611* (2013.01); *A61F 2/4465* (2013.01); *A61F 2002/30133* (2013.01); *A61F 2002/30538* (2013.01); *A61F 2002/4625* (2013.01)

(58) Field of Classification Search
CPC .................. A61F 2/46; A61F 2/4611
See application file for complete search history.

(56) References Cited

U.S. PATENT DOCUMENTS

| 7,892,239 B2* | 2/2011 | Warnick | A61F 2/4465 606/279 |
| 2005/0096745 A1 | 5/2005 | Andre et al. | |
| 2007/0093897 A1* | 4/2007 | Gerbec | A61F 2/4465 623/17.11 |
| 2012/0130387 A1* | 5/2012 | Simpson | A61F 2/4611 606/104 |

FOREIGN PATENT DOCUMENTS

DE     WO2013149611      10/2013

* cited by examiner

*Primary Examiner* — Christopher J Beccia
(74) *Attorney, Agent, or Firm* — Mark Wisnosky

(57) ABSTRACT

The invention relates to an operating instrument for minimally invasive or conventional implanting of a spinal implant into the intervertebral space comprising an outer tube which has a hollow handle on its proximal end, wherein the inner rod can be moved in the outer tube and the hollow handle, and the inner rod is provided with a threaded region which extends beyond the distal end of the outer tube, wherein the threaded region serves for fastening to the rear region of an implant and for tensioning the implant with its rear region against the distal end region of the outer tube, wherein the distal end region of the outer tube is at least partially adapted to the rear region of the implant, wherein the tensioning of the implant against the outer tube takes place by means of a tensioning device having a lever.

12 Claims, 7 Drawing Sheets

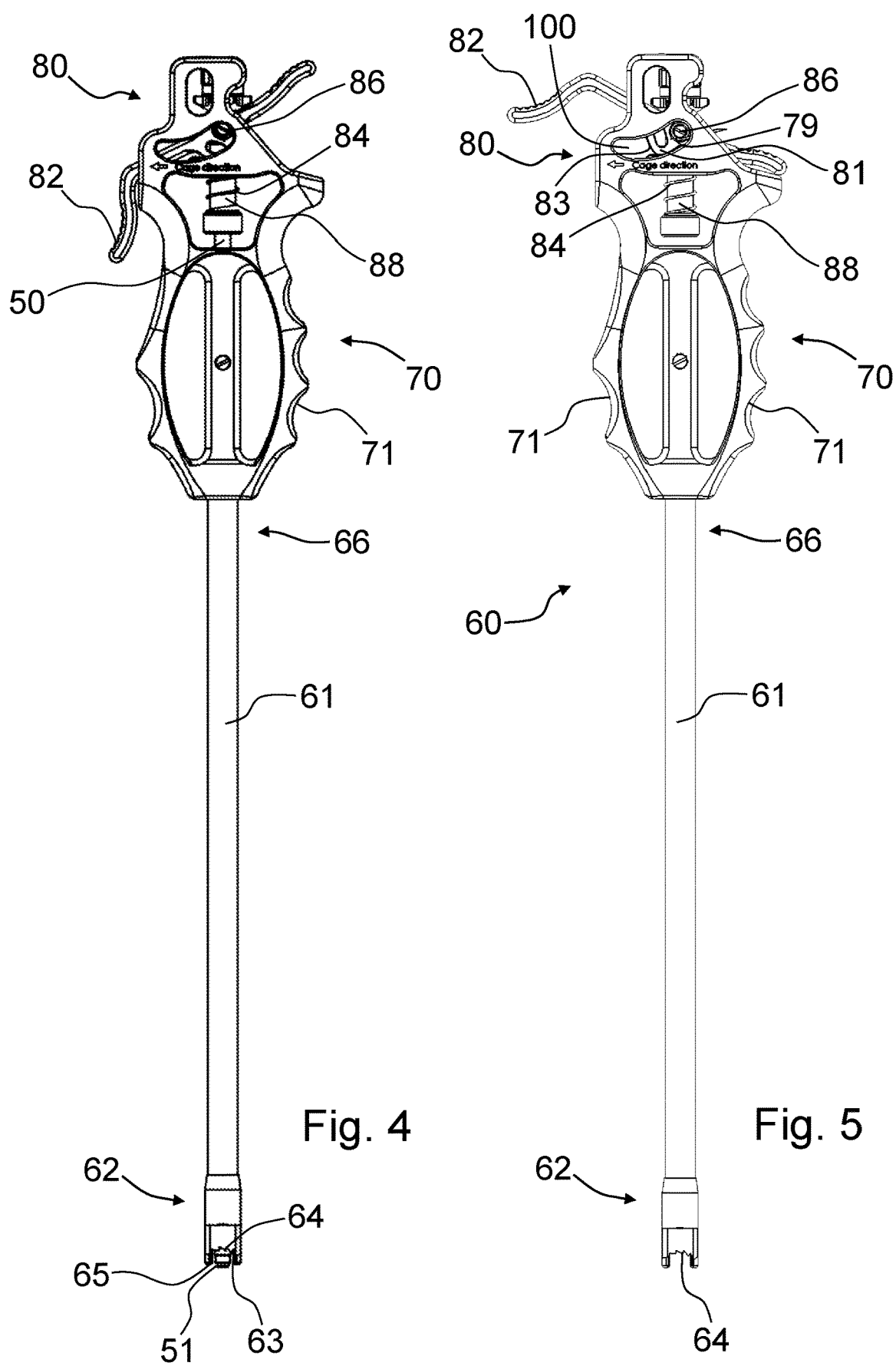

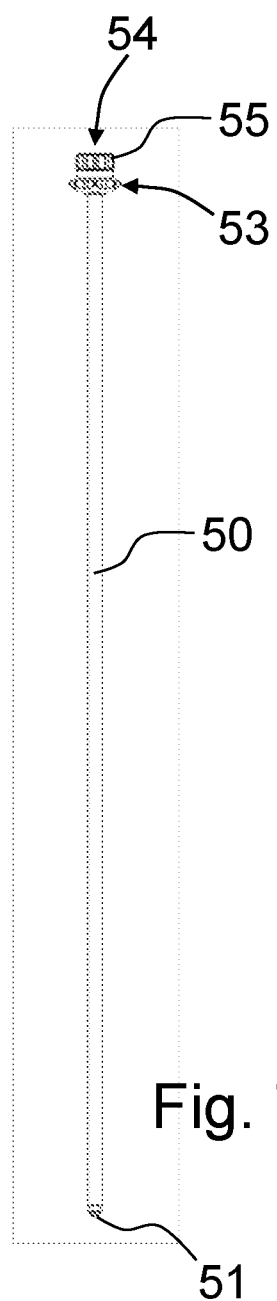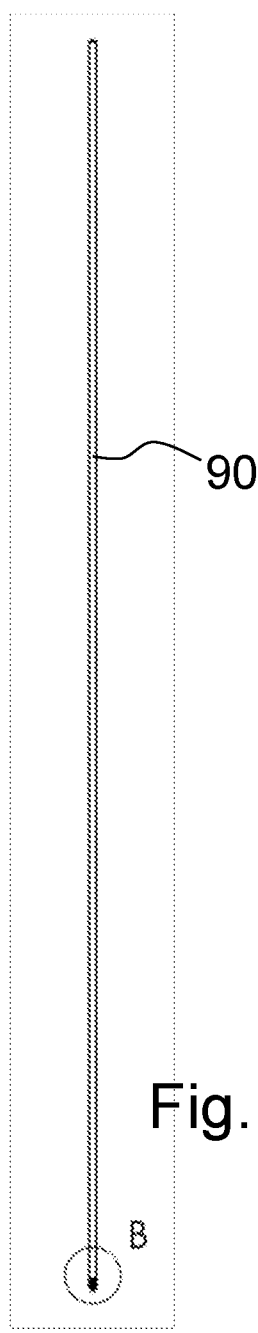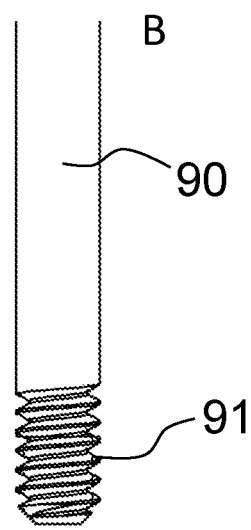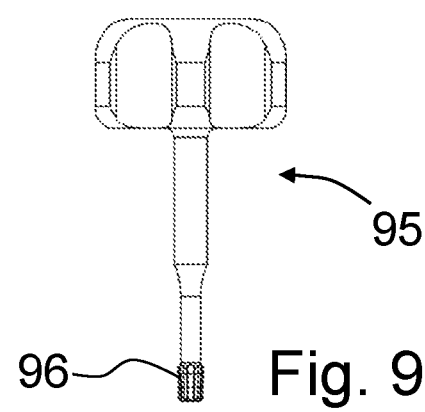
Fig. 7
Fig. 8A
Fig. 8B
Fig. 9

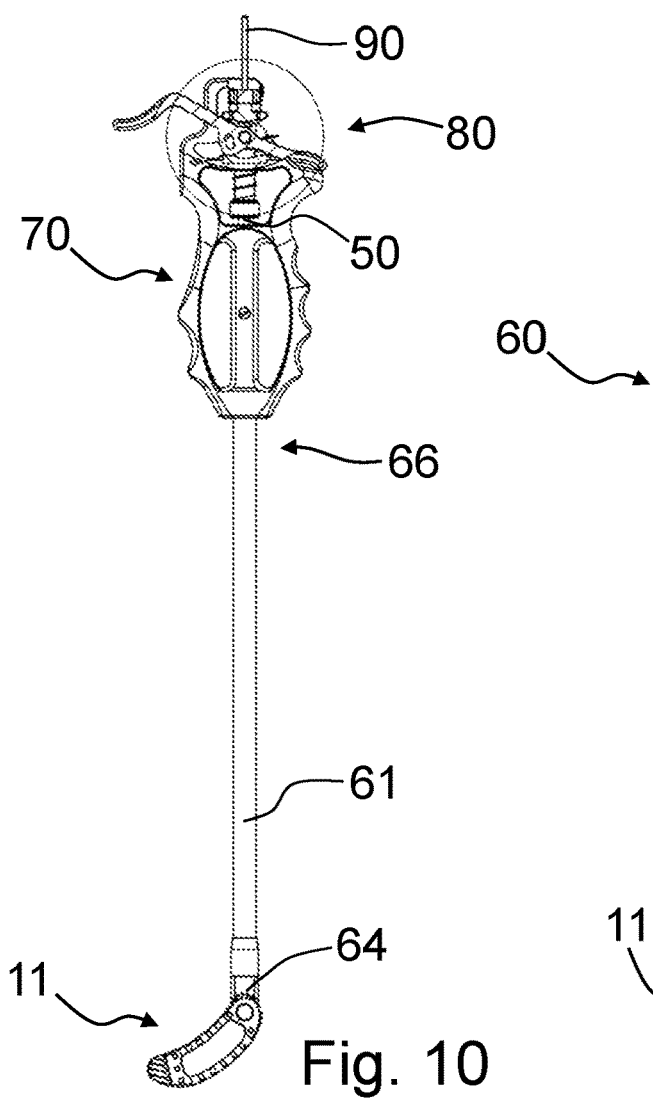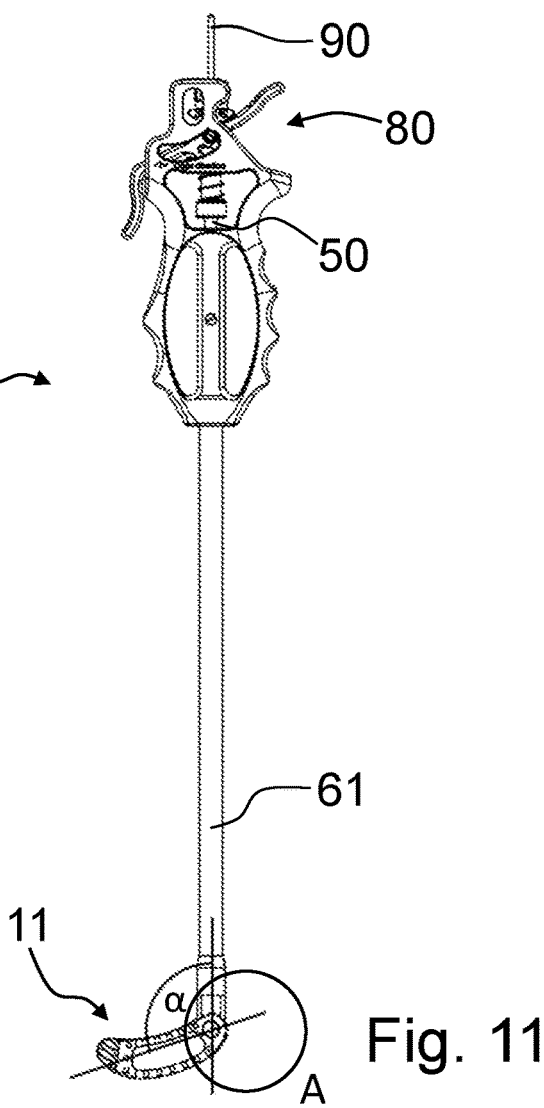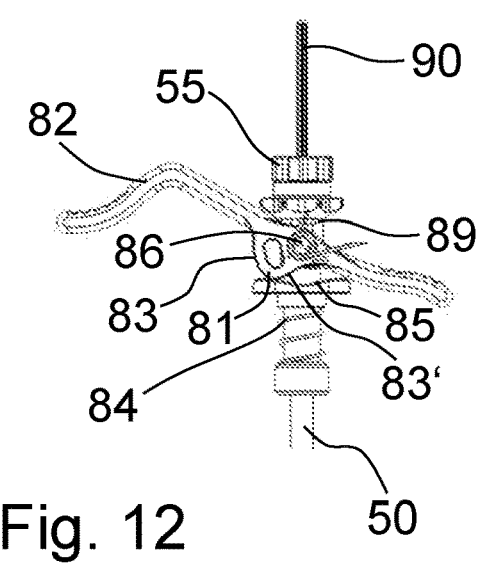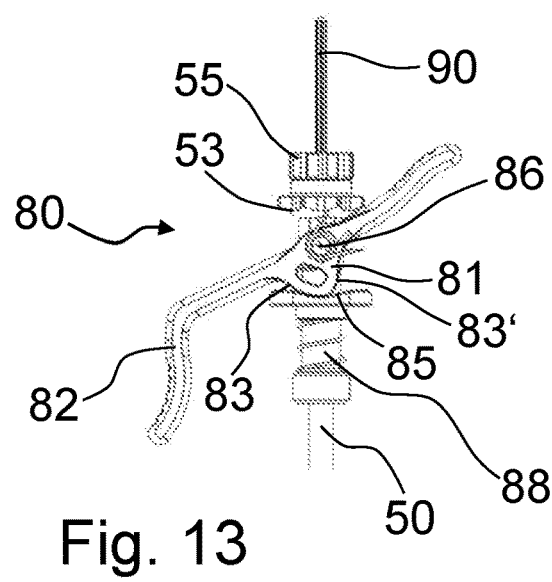

INSTRUMENT FOR INSERTING A SPINAL IMPLANT AND A SPINAL IMPLANT

CROSS-REFERENCE TO RELATED APPLICATIONS

This application claims priority to German patent application 10 2016 113 488.0, titled: Instrument for inserting a spinal implant and a spinal implant, Filed 21 Jul. 2016.

STATEMENT REGARDING FEDERALLY SPONSORED RESEARCH OR DEVELOPMENT

Not Applicable.

BACKGROUND OF THE INVENTION

Technical Field

The present invention relates to operating instruments and spinal implants adapted thereto which can be inserted into the intervertebral space from all usual, conventional, and less or minimally invasive access variants and, for example in the case of TLIF or PLIF, can be brought into the optimal permanent position locally in a mechanically safe manner.

Related Background Art

In the event of advanced degeneration of intervertebral discs in the lumbar spine region, stiffening surgery is often the best option for treatment. For this, the remains of the worn intervertebral discs are removed, and bone or bone replacement material is inserted into the defect with the aim of a fusion, i.e. the adjacent vertebrae joining to form a block. First of all, it is important to ensure the mechanical stability required for bone healing, and secondly, to restore the geometrical (=anatomical) conditions which are necessary for undisturbed nerve function. In order to ensure this, placeholder implants, so-called "cages", have been used all over the world for the reconstruction of the vertebral body column which is located in front of the thecal sac. The direct implantation path to this leads accordingly through the abdomen and is used when conventionally open (anterior lumbar interbody fusion, ALIF) or even minimally invasive (e.g. XLIF, OLIF) surgical access techniques are used. However, because most of these pathologies also require surgical procedures to the structures which are dorsal of the spinal canal, the question arises as to whether the additional anterior procedure cannot be avoided, and the reconstructive measures of the anterior column can be carried out from dorsal, past the thecal sac and the nerve roots. The corresponding surgical procedures (posterior lumbar interbody fusion, PLIF, and transforaminal interbody fusion, TLIF), are established and clinical routine. Due to the tight anatomical space conditions, smaller cages are introduced from dorsal at the side of the thecal sac into the former intervertebral disc space. The direction of the access path thus dictates the permanent position of the implant. In most of these cage provisions, the fact that lumbar intervertebral discs are higher at the front than at the back, which results in a normal profile, "lordosis", and the fact that an implant having as large an area as possible with a position near and parallel to the front edge ensures optimal load transfer, remain disregarded or poorly reconstructed.

The implants are inserted from a dorsal access into the space between the adjacent vertebrae after the removal of the intervertebral disc space and can then be rotated or pivoted into the coronal plane. Here, the convex region of the cage should be positioned in parallel to the front boundary of the intervertebral disc space.

In order to safely insert the implant into the intervertebral space, the implant should firstly be connected as rigidly as possible to the insertion tool. The implant is hingedly fastened to the distal end of an operating instrument for this purpose. By means of a screw mechanism, which is provided at the proximal end of the operating instrument, the implant can be pulled into coaxial alignment against the distal end of the tubular operating instrument and locked there in an angularly stable manner. Subsequently, the implant can be inserted, if necessary driven, into the intervertebral space under the protection of dura and emerging nerve root. Here, grooves form the path on the contact surfaces to the adjacent vertebrae and the specifically shaped implant tip (bullet nose). After passing the neural structures, the operating instrument, as far as possible, is pivoted in the transverse plane, the tension in the hinge is released by turning the handle, and the instrument is moved to the other side of the wound by pivoting.

In this modified position with respect to the operating instrument, the hinge connection to the implant is locked again by tensioning the locking lever, and the operating instrument is rotated back into the original position. This pivoting process is repeated until the implant in the former intervertebral disc space is rotated from the sagittal direction into the coronal plane.

This is described, for example, in DE 10 2013 005 692 A1 or EP 2 419 033 B1.

An arched interbody cage is known from WO 2005/041825 A1, which has a breakthrough at its two ends and a groove which leads into the breakthrough and serves for the engagement between a bar and a fastening cam, wherein the fastening cam can be moved in a groove in the cage. By actuating a screw mechanism, the cage can then additionally be firmly screwed to the operating instrument such that a rigid connection is established between the cage and the fastening device, and the cage can thus be driven into the intervertebral space. In order to release this rigid connection, the knurled screw is loosened again, the angle between the longitudinal axis of the cage and the longitudinal axis of the operating instrument is modified, and then the cage can be inserted further into the intervertebral space.

DE 10 2013 005 692 A1 discloses a tool with two different inserts for inserting spinal implants. The operating instrument, an insertion rod, comprises an outer tube which has a hollow handle on its proximal end for receiving a first inner rod. The inner rod is provided with a threaded region which extends beyond the distal end of the outer tube. The threaded region on the inner rod serves for fastening to the rear region of the implant which has a corresponding threaded bore there. The rear region of the implant can also be tensioned against the distal end region of the outer tube by means of the inner rod which can be moved with respect to the outer tube. For this purpose, the distal end region of the outer tube is at least partially adapted to the rear region of the implant. Locking is carried out by actuating a screw thread.

The previously described insertion tool is used to insert the cage into the intervertebral disc space until its rear end is at the level of the annulus of the intervertebral disc, said tool being unscrewed and exchanged for a special "ball" tool when the desired position is reached in order to drive the cage further in and at the same time to enable rotation/pivoting.

The need for several tools is cumbersome and increases the risk for the nerve structures that must be passed through during each change. In addition, control of the current implant position is temporarily lost in the depth of a (bleeding) wound, and, in some instances, the implants cannot be positioned in the exactly desired position with the tools known to date. In some implants, there is also the risk that they may become detached from the operating instrument during surgery. Once the implant has been inserted and detached from the operating instrument, it is also difficult to dock it back on the operating instrument for repositioning. Control over the movement of the implant is also difficult. In addition, the operating instrument interferes with an X-ray examination.

If it is necessary to change to another implant size, the guided and safe possibility for removal is not available.

BRIEF SUMMARY OF THE INVENTION

The object of the present invention consists in providing an operating tool and a spinal implant which permit an implantation which is safe, simple and causes as little trauma as possible.

This object is solved by the features of claims 1, 10 and 12.

According to the invention, provision is made for the implant to be tensioned with the outer tube of the operating instrument by means of a tensioning device having a lever, so as to enable a quick and easy releasing and locking of the tensioning of the distal end of the rear part of the implant with respect to the distal end of the outer tube.

The tensioning device can be operated by a simple actuation of a lever such that the time-consuming and cumbersome screwing and releasing of the previously known screw connections is avoided.

The tensioning device according to the invention has a locked position and a released position. When the lever of the tensioning device is actuated, the inner tube in the outer tube is moved from a released position into a locked position, in which the rear region of the implant is tensioned with the distal end region of the outer tube.

The tensioning device preferably comprises a lever with an eccentric.

In order to achieve particularly simple and safe operation, the tensioning device is preferably self-locking, such that devices which ensure fixing in the locked position can be dispensed with.

The lever is particularly preferably arranged on the handle or on a tubular piece which can be moved with respect to the handle. The lever can be put back into the released position by means of corresponding spring elements or by hand.

In a preferred variant, the lever of the tensioning device is fastened to a tubular piece which can be moved in the longitudinal direction, in which tubular piece the inner rod is guided, wherein the proximal end of the inner rod lies on the proximal end of the tubular piece. By actuating the lever, the tubular piece and thus the inner rod lying on the tubular piece are moved in the proximal direction with respect to the handle, and the implant is tensioned against the distal end of the inner rod, for example by the eccentric.

The movement of the implant in the direction of the distal end of the outer tube and the tensioning thus take place only by pressing down the lever.

A spring element can also be provided on the tubular piece, said spring element serving to locate the normal position in which the implant can be placed.

The present invention also relates to an operating instrument in which the inner rod is hollow and in which a further holding rod is provided which serves to fix the implant alone during the X-ray examination, wherein the holding rod can be received in the hollow inner rod. Due to the fact that the inner rod is hollow, a holding rod can be pushed into the hollow inner rod and screwed to the implant before the X-ray examination. Subsequently, the entire operating instrument is removed except for the holding rod which is screwed to the implant, and the position of the implant is examined by means of X-ray with the thin holding rod attached thereto. After that, the entire operating instrument can be pushed back onto the holding rod over the holding rod and the operating instrument can be reattached to the implant. The implant can thus no longer be lost in the intervertebral space.

This aspect of the invention is independent of the other special design of the operating instrument and in particular of the presence of a tensioning device.

In a preferred embodiment, the holding rod has a threaded region on its distal end for fastening to the implant.

The invention as well as further advantageous embodiments and further developments thereof are described and explained in more detail below with reference to the examples shown in the drawings. The features to be taken from the description and the drawings can be applied individually or together in any combination according to the invention.

BRIEF DESCRIPTION OF THE DRAWINGS

Here are shown.

DETAILED DESCRIPTION OF THE INVENTION

Figure 1:
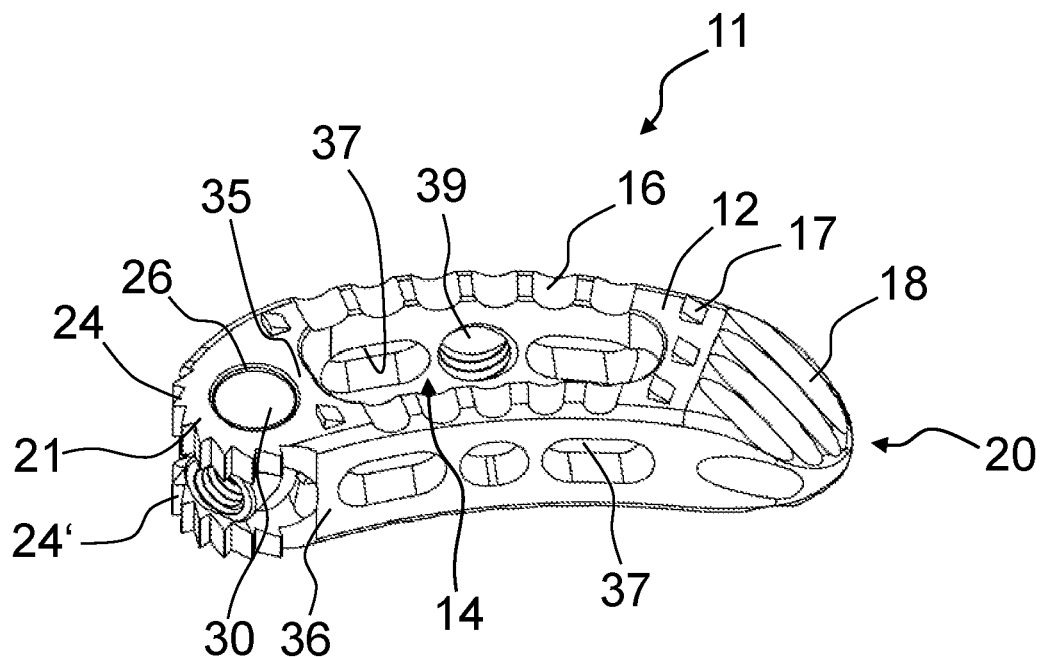
FIG. 1 the top view of an implant from above,
FIG. 2 a side view of the implant from FIG. 1 on the concave side,
FIG. 3 a side view of the implant from FIG. 1 on the convex side,
FIG. 4 the side view of the operating instrument with a hollow inner rod,
FIG. 5 the side view of the operating instrument without a hollow inner rod,
FIG. 6 the side view of the operating instrument with a hollow inner rod and holding rod,
FIG. 7 a side view of the hollow inner rod,
FIG. 8A a side view of the holding rod,
FIG. 8B an enlarged depiction of region B from FIG. 8A,
FIG. 9 a side view of the wrench,
FIG. 10 the operating instrument with the implant in the released position,
FIG. 11 the operating instrument with the implant from FIG. 10, but in the locked position,
FIG. 12 a side view of the tensioning device in the released position without the handle,
FIG. 13 a side view of the tensioning device in the locked position without the handle and
FIG. 14 a detailed view of region A in FIG. 11, but at a different angular position of the implant.
Figure 2:
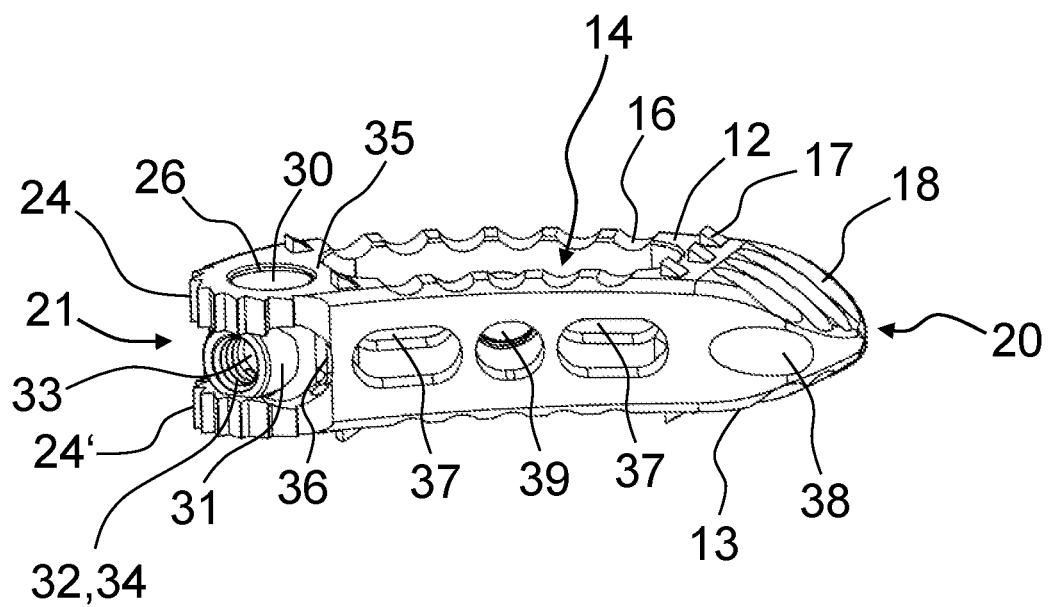
Figure 3:
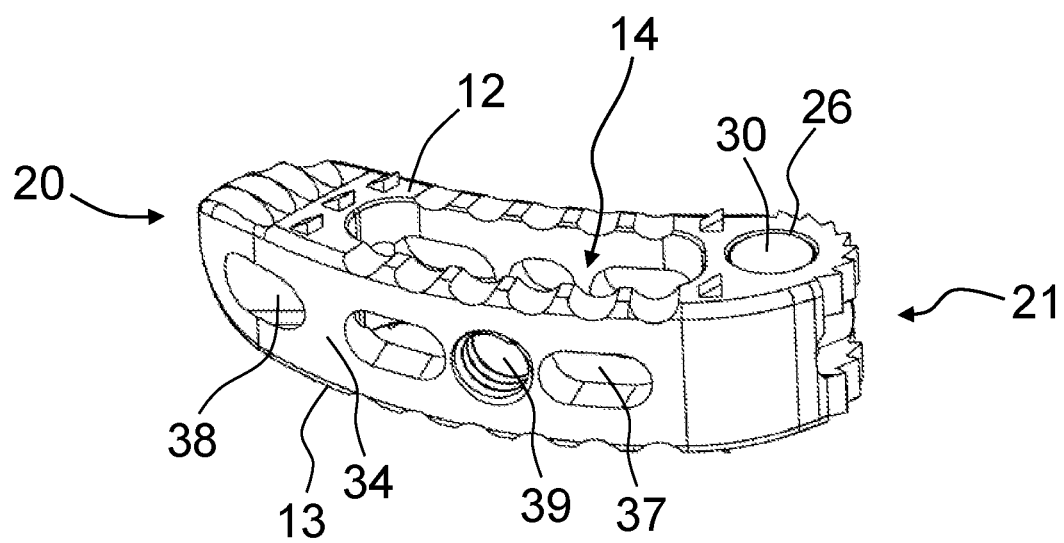

The implant 11 in FIGS. 1, 2 and 3 has an elongated, slightly curved banana-shaped form with an upper side 12 and a lower side 13. A vertically extending passage opening 14 extends through the upper 12 and lower side 13 of the implant 11, said passage opening 14 extending in the central region of the implant 11 and serving to receive bone material and for better ossification. Due to their cage-like appearance, such implants 11 are also referred to as "cages".

Furthermore, there are grooves 16 and mandrels 17 on the upper 12 and lower side 13 of the implant 11, which serve to improve the fixing of the implant 11. The grooves are arranged obliquely in order to bring the implant 11 into a radius and finally into the 90° position when it is inserted.

The two lateral ends 20, 21 of the implant 11 are different. The implant 11 is chamfered on one lateral end 20, the front end, and the upper 12 and lower side 13 extend towards one another. This end 20 is formed to be wedge-shaped ("bullet nose") and rounded, such that the implant 11 can be inserted into the intervertebral space with this end 20. Grooves 18 also extend on the upper 12 and lower side 13 of the front end 20.

The other end of the implant 11, the implant rear 21, is rounded when seen from above and has a sprocket 24, 24' on both the upper 12 and lower side 13. The space between the upper side 12 and the lower side 13 on the implant rear 21 is substantially open. In addition, two bores 26, which align and in which a cylindrical cone 30 is pivotally guided, are located in the upper 12 and lower side 13. A threaded piece 31 extends radially outwards from the outer surface of the cone 30 in the horizontal direction, said threaded piece 31 having an internal thread 32 with a larger diameter and an internal thread 33 with a smaller diameter. The internal thread 32 with the larger diameter serves for fastening to the distal end of the outer tube 61 and the internal thread 33 with the smaller diameter for fastening the distal end of the holding rod 90 which, if desired, is pushed into the outer tube 61 and, with its distal end, can be screwed to the internal thread 33 with the smaller diameter.

The internal thread 33 with the smaller diameter extends from the end of the internal thread 32 with the larger diameter further into the cone 30.

The cone 30 with the threaded piece 31 can be pivoted in the bores 26 at an angle of at least 50° and preferably at least 60° with respect to the implant 11 because the implant 11 is substantially open in the pivoting region between the upper side 12 and the lower side 13. The pivoting movement of the cone 30 with the threaded piece 31, which takes place in a type of groove, is laterally limited by the side wall 36 of the implant 11, which forms a stop.

A continuous wall 35, extending from the upper 12 to the lower side 13 of the implant 11, provides the rear region 21 of the implant 11 with the required stability on the side of the cone 30 facing towards the passage opening 14.

In the lateral outer walls 34, 36 of the implant 11, which connect the upper 12 and the lower side 13 of the implant 11, openings 37 are also provided which serve for better ossification.

The convex side wall 34 is slightly higher than the concave side wall 36 because of the desired lordosis shape.

Openings 38 extending horizontally, which extend from the wedge-shaped front end 20 (bullet nose) in the direction of the vertically extending passage opening 14 of the implant 11, are also provided, which also serve for better ossification.

In the convex side wall 34 of the implant 11, a receiving opening 39 is provided which has an internal thread. After the operating instrument 60 or a further conventional insertion instrument has been screwed into the receiving opening 39, this also allows the implant 11 to be introduced from the ventral direction. After implantation, the receiving opening 39 also serves for better ossification.

Figure 6:
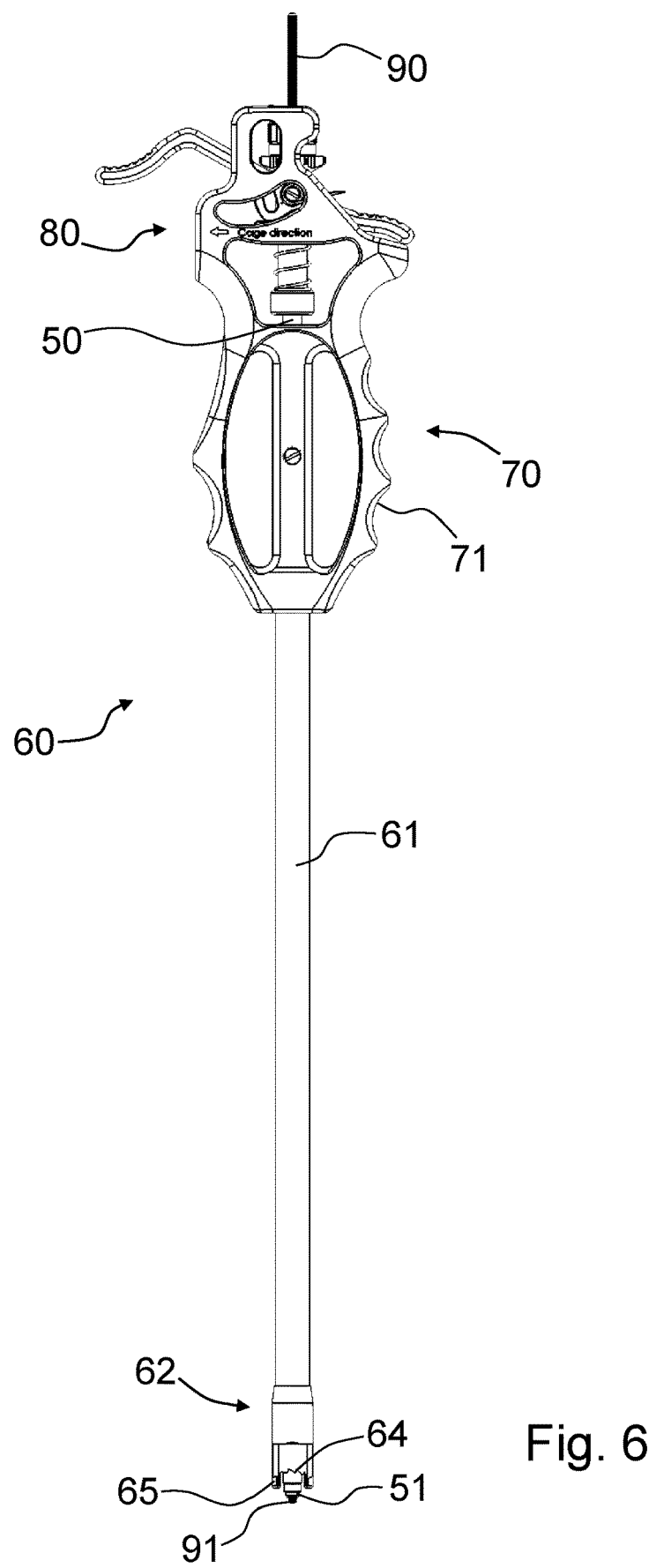
Figure 14:
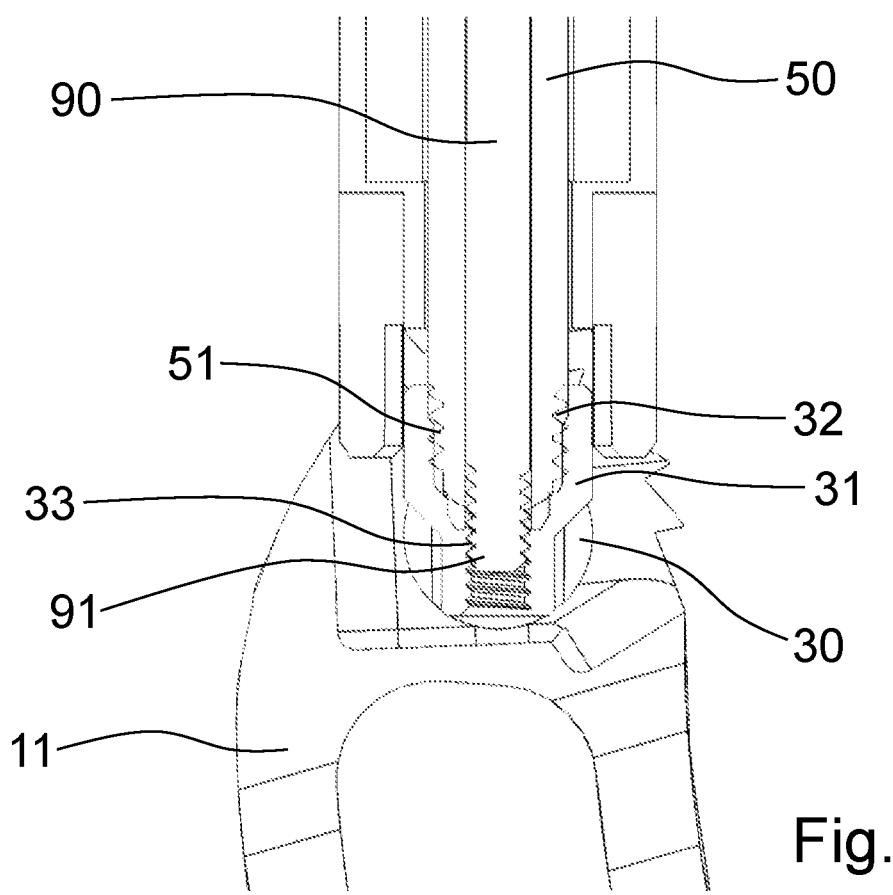

The operating instrument 60, which is shown in FIGS. 4 to 6, comprises a long outer tube 61, which, at its distal end 62, has a recess 63 corresponding to the rounded shape of the implant rear 21, having a sprocket 64 corresponding to the sprocket 24, 24' at the rear region 21 of the implant 11. The distal end region of the outer tube 61 is thus at least partially adapted to the rear region 21 of the implant 11. The teeth of the sprockets 24, 24' on the implant 11 and on the sprocket 64 of the operating instrument 60 engage with one another in order to achieve as stable a connection as possible. In order to facilitate, on the one hand, the rotational movement of the implant 11 with respect to the operating instrument 60 during pivoting, and in order to avoid, on the other hand, a possible backwards movement of the implant 11 during the rotation process in the coronal plane, the teeth of the sprocket 24, 24', 64 are asymmetrical. Two pins 65 extending in the longitudinal direction are also provided on the distal end 62 of the outer tube 61, which primarily serve to not lose alignment in the released state, such that the teeth can be found again during reattachment and serve in addition to encompass the threaded piece 31 laterally.

At the proximal end 66, the outer tube 61 passes into the handle 70, which has several gripping recesses 71, such that it can be completely encompassed by the hand and is well positioned in the hand. The tensioning device 80 is located in the proximal end region of the handle 70 for tensioning the inner rod 50.

The inner rod 50 is moveably guided in the outer tube 61. In this embodiment, the inner rod 50 is formed as a hollow inner rod 50, i.e. as an inner tube. The inner tube 50 is provided on its distal end with an external thread 51 which extends beyond the distal end of the outer tube 61 and can be screwed to the internal thread 32 with a larger diameter in the threaded piece 31 of the cone 30 in the implant 11.

Once screwing has taken place, the implant 11 is captively fastened to the inner tube 50, but can be pivoted with respect to this as a result of the pivotable cone 30.

By actuating the tensioning mechanism 80, the sprocket 64 on the distal end 62 of the outer tube 61 can be brought into engagement with the sprocket 24, 24' in the rear region 21 of the implant 11. Furthermore, the two pins 65 encompass the threaded piece 31 on the pivotable cone 30 on the right and left sides, such that the implant rear 21 with the sprocket 24, 24' is rigidly connected to the outer tube 61. In addition, the outer tube 61 is also rigidly connected to the threaded piece 31 and the cone 30 via the pins 65. Since the inner tube 50 is also rigidly connected to the threaded piece 31 of the cone 30 via the screw connection 51, 32, the cone 30 can also no longer be pivoted back and forth.

In this locked position, which corresponds to the tensioned tensioning device 80, and in which the screw threads 51, 32, sprockets 24, 24', 64 and pins 65 are all brought into engagement, the implant 11 is rigidly and securely fastened to the operating instrument 60.

Therefore, in the locked state, a rigid connection between the implant 11 and the operating instrument 60 is achieved, and the implant 11 can be inserted safely into the cleared out intervertebral space.

As soon as the implant 11 reaches the position required for the required pivoting movement and has been jammed between the adjacent vertebrae, the rigid connection between the sprockets 24, 24', 64 can be released by loosening the tensioning mechanism 80, and the pins 65 encompassing the threaded part 31 on the outside are removed again from the threaded piece 31. In this "released position", the implant 11 is only fastened to the outer tube 61 of the operating instrument 60 by means of the screw connection 32, 51 on the cone 30, and a pivoting movement of the operating instrument 60 with respect to the implant 11 is now also possible as a result of the pivotability of the implant 11 with respect to the cone 30.

Therefore, by releasing the tensioning device 80 and thus reproducing the movability of the operating instrument 60 with respect to the implant 11 which is fixed in the intervertebral space, the angle α between the longitudinal axis of the outer tube 61 (see FIG. 11) and the longitudinal axis of the implant 11 can be slightly reduced. The implant 11 is now rigidly reconnected to the operating instrument 60 by tensioning the tensioning device 80, the operating instrument 60 is now pivoted or levered again in the operation opening until it reaches the edge of the operation opening. The tensioning device 80 is reopened and the angle α is reduced in turn, the implant 11 is fastened again, and another piece is rotated again in the transverse plane until the implant 11 is pivoted parallel to the front edge after several repetitions of this process. The correct positioning is controlled by an intraoperative X-ray image. For this purpose, the operating instrument 60 is designed in such a way as to avoid the implant position being lost in the meantime or the operating instrument 60 protruding from the body accidentally being moved into the spinal canal during X-ray and/or triggering a higher radiation dose. For this purpose, a holding rod 90 is initially introduced through the inner rod 50, which is formed to be hollow as an inner tube 50 for this purpose, wherein an external thread 91 having a small diameter is located on the distal end of said holding rod 90. The external thread 91 of the holding rod 90 can be screwed to the internal thread 33 with the smaller diameter in the threaded piece 31 such that the implant 11 can be fastened to the holding rod 90. Subsequently, the entire operating instrument 60 (i.e. with the outer tube 61 and the inner tube 50) can be removed from the implant 11, except for the holding rod 90, which remains attached to the implant 11 via the internal thread 33 in the threaded piece 31 such that the position of the implant 11 cannot be lost during X-ray. The diameter of the holding rod 90 is small and is only approximately 1 to 2 mm, such that the X-ray image is only insignificantly disturbed.

If the X-ray image shows that the implant 11 must be inserted further or the position of the implant must be changed, then the operating instrument 60 having the inner tube 50 and the outer tube 61 encompassing the inner tube 50 is again slipped over the proximal end of the holding rod 90 and the inner tube 50 is again fastened with its distal end 51 to the internal thread 32 of the threaded piece 31 of the implant 11.

When the tensioning device 80 is released, the angle between the implant 11 and the operating instrument 60 can be changed again, the tensioning device 80 can be tensioned again etc. and the implant 11 can be brought into the next desired position.

The tensioning device 80 is on the proximal end 66 of the operating instrument 60, by means of which tensioning device 80, in the simplest variation, the implant 11 fastened to the inner tube 50 is pressed with its sprocket 24, 24' against the sprocket 64 located on the distal end of the outer tube 61 and can thus be brought into engagement with this.

The tensioning device 80 is a clamping device which can be released and fixed by actuating a lever 82 and preferably transfers into self-locking.

In the preferred variants shown in FIGS. 4 to 14, the tensioning device 80 can be actuated by means of a two-sided lever 82, which is rotatably fastened approximately centrally on an axis of rotation 86 and can be pivoted from the released position (FIG. 10, FIG. 12) into the locked position (FIG. 11, FIG. 13) and then released again. The lever 82 can be put back into the released position by means of corresponding spring elements 79 or by hand.

There is an eccentric 81 on the lower side of the lever 82, said eccentric 81 being integrally connected to the lever 82. The eccentric 81 lies with its lower side 83 on a sliding surface 85 of the handle piece 70. When the lever 82 is actuated, increasing tension now results by means of the tensioning surfaces 83, 83' of the eccentric 81 which are increasingly spaced apart with respect to the axis of rotation 86 and which slide along the sliding surface 85 of the handle 70, said tension transferring to self-locking as a result of friction.

In the preferred variant, the axis of rotation 86 and the lever 82 are fastened to a moveable tubular piece 88 such that, upon actuation of the lever 82 (tensioning) by the eccentric 81, the entire moveable tubular piece 88 including the lever 82 is moved and fixed in the proximal direction. However, after the inner tube 50 has been inserted into the moveable tubular piece 88 at the proximal end of the moveable tubular piece 88, and the inner tube 50 has a stop 53 which is supported on the outer edge 89 of the tubular piece 88, not only the moveable tubular piece 88 but also the inner tube 50 is pushed in the proximal direction when the lever 82 is actuated, and as a result the implant 11 which is screwed to the distal end 51 of the inner tube 50 is pressed against the distal end of the outer tube 61 and the sprocket 64 there and is brought into engagement with this such that, in the locked position, the angular position of the implant 11 is fixed with respect to the outer tube 61.

By actuating the lever 82 of the tensioning device 80, a rigid fastening between the implant 11 and the operating instrument 60 can thus be provided in a quick and easy manner, said fastening being able to be released again in a quick and easy manner by loosening the tensioning device 80, i.e. actuating the other side of the lever 82.

In order to return the inner tube 50 to the original position after releasing the tensioning device 80, the tensioning device 80 is fastened to the moveable tubular piece 88 which, in the distal direction, has a stop for a spring 84 which encompasses the outer surface of the tubular piece 88. On the other side, the spring 84 rests against the handle 70. When the tensioning device 80 is released, the spring 84 on the moveable tubular piece 88 causes the tubular piece 88 and thus the inner tube 50 to be moved in the distal direction and thus to be brought into the released position.

The spring 84 provided on the tubular piece 88 therefore disengages the outer tube 61 from the rear region 21 of the implant 11 again in the released position.

Instead of the stop 53 on the inner tube 50, an operating wheel can also be provided which enables the degree of screwing of the outer thread 51 of the inner tube 50 into the internal thread 32 of the implant 11. The more deeply the thread 51 is screwed into the thread 32, the more force must be applied when actuating the lever 82, and the more quickly the tensioning device 80 becomes self-locking.

A rotary disk 55 is screwed onto the proximal end of the inner tube 50 for the fine adjustment of the tension between the inner and outer tubes.

In order to screw the inner tube 50 (and also the holding rod 90) to the implant 11 in a simple manner, the inner tube 50 has a receiver 54 on its proximal end for the carrier profile 96 of a screwdriver 95 (see FIG. 9), by means of which the inner tube 50 can be screwed to the implant 11 in a simple manner. The screw connection can also occur when the holding rod 90 is additionally inserted into the inner tube 50.

Once the sprockets 24, 24', 64 are asymmetrical, it is necessary to screw the implant 11 onto the operating instrument 60 in a certain direction. In order to illustrate the position of the implant 11, the location of the implant 11 in the handle region is shown by a corresponding display 100.

What is claimed is:

1. Operating instrument for implanting a spinal implant, comprising an outer tube having a proximal and a distal end, which has a hollow handle on its proximal end, wherein an inner rod can be moved in the outer tube and the hollow handle, and the inner rod having a threaded region which extends beyond the distal end of the outer tube, wherein the threaded region serves for fastening to a rear region of an implant and for tensioning the implant with its rear region against the distal end of the outer tube, wherein the distal end of the outer tube is at least partially adapted to the rear region of the implant, characterised in that the inner rod is hollow and a further holding rod, having a proximal and distal end, is provided which serves, upon removal of the inner tube and the outer tube, to fix the implant alone during X-ray examination, wherein the holding rod can be received in the hollow inner rod.

2. Operating instrument according to claim 1, characterised in that the holding rod has a threaded region on its distal end for fastening to the implant.

3. Spinal implant for use with an operating instrument according to claim 1, having an upper side and a lower side, a vertical passage opening, a front end and an implant rear which has a moveable cone having a threaded piece, characterised in that the threaded piece has an internal thread having a larger diameter for fastening the inner rod and a threaded piece having a smaller diameter for fastening the holding rod.

4. Operating instrument according to claim 1, characterised in that the tensioning of the implant against the distal end of the outer tube takes place by means of a tensioning device having a lever.

5. Operating instrument according to claim 4, characterised in that the tensioning device has a locked position and a released position and, upon actuation of the lever of the tensioning device, the inner tube in the outer tube is moved from a released position into a locked position, in which the rear region of the implant is tensioned against the distal end of the outer tube.

6. Operating instrument according to claim 4, characterised in that the tensioning device lever having an eccentric, the lever is hingedly connected to a tubular piece and, upon actuation of the lever, the tubular piece is moved in a longitudinal direction and locked.

7. Operating instrument according to claim 4, characterised in that the lever is put back into the released position by means of spring elements.

8. Operating instrument according to claim 4, characterised in that the tensioning device is self-locking.

9. Operating instrument according to claim 4, characterised in that the lever is arranged on the handle or a tubular piece which can be moved with respect to the handle.

10. Operating instrument according to claim 9, characterised in that a stop lies on the tubular piece on the proximal end of the inner rod and the inner rod is guided in the tubular piece and the tubular piece can be moved in the longitudinal direction with respect to the handle.

11. Operating instrument according to claim 9, characterised in that a spring element provided on the tubular piece disengages the inner rod from the rear region of the implant in the released position.

12. Operating instrument according to claim 10, characterised in that a spring element provided on the tubular piece disengages the inner rod from the rear region of the implant in the released position.

* * * * *